(12) United States Patent
Belcheva et al.

(10) Patent No.: US 8,487,017 B2
(45) Date of Patent: Jul. 16, 2013

(54) BIODEGRADABLE MATERIALS FOR ORTHOPEDIC DEVICES BASED ON POLYMER STEREOCOMPLEXES

(75) Inventors: Nadya Belcheva, Hamden, CT (US); Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/169,539

(22) Filed: Jun. 27, 2011

(65) Prior Publication Data

US 2012/0329901 A1  Dec. 27, 2012

(51) Int. Cl.
*A61L 24/00* (2006.01)

(52) U.S. Cl.
USPC .......................... 523/113; 523/105; 523/115

(58) Field of Classification Search
USPC ........................................ 523/105, 113, 115
See application file for complete search history.

(56) References Cited

U.S. PATENT DOCUMENTS

| | | | |
|---|---|---|---|
| 3,364,200 A | 1/1968 | Ashton et al, |
| 4,626,253 A | 12/1986 | Broadnax, Jr. |
| 4,719,246 A | 1/1988 | Murdoch et al. |
| 4,766,182 A | 8/1988 | Murdoch et al. |
| 4,800,219 A | 1/1989 | Murdoch et al. |
| 4,981,696 A | 1/1991 | Loomis et al. |
| 5,317,064 A | 5/1994 | Spinu |
| 5,484,913 A | 1/1996 | Stilwell et al. |
| 5,521,360 A | 5/1996 | Johnson et al. |
| 5,663,237 A | 9/1997 | Lee et al. |
| 5,698,762 A | 12/1997 | Dauerman |
| 5,782,908 A | 7/1998 | Cahalan et al. |
| 6,150,459 A | 11/2000 | Mayes et al. |
| 6,175,037 B1 | 1/2001 | Tweedy |
| 6,207,749 B1 | 3/2001 | Mayes et al. |
| 6,306,424 B1 | 10/2001 | Vyakarnam et al. |
| 6,333,029 B1 | 12/2001 | Vyakarnam et al. |
| 6,358,557 B1 | 3/2002 | Wang et al. |
| 6,365,149 B2 | 4/2002 | Vyakarnam et al. |
| 6,365,173 B1 | 4/2002 | Domb et al. |
| 6,383,500 B1 | 5/2002 | Wooley |
| 6,399,700 B2 | 6/2002 | Mayes et al. |
| 6,413,539 B1 | 7/2002 | Shalaby |
| 6,443,964 B1 | 9/2002 | Ory et al. |
| 6,469,133 B2 | 10/2002 | Baker et al. |
| 6,500,777 B1 | 12/2002 | Wiseman et al. |
| 6,534,084 B1 | 3/2003 | Vyakarnam et al. |
| 6,870,003 B2 | 3/2005 | Nishikawa et al. |
| 7,021,086 B2 | 4/2006 | Ory et al. |
| 7,112,417 B2 | 9/2006 | Vyakarnam et al. |
| 7,141,769 B2 | 11/2006 | McManus et al. |
| 7,217,750 B2 | 5/2007 | Gencer et al. |
| 7,348,182 B2 | 3/2008 | Martin et al. |

(Continued)

OTHER PUBLICATIONS

Jérôme et al. "Recent Advances in Synthesis of Aliphatic Polyesters by Ring-Opening Polymerization," Advanced Drug Delivery Review 60 (2008), pp. 1056-1076.

(Continued)

*Primary Examiner* — James J Seidleck
*Assistant Examiner* — Peter A Salamon

(57) ABSTRACT

An implantable orthopedic medical device is disclosed. The medical devices is formed from a biodegradable polymer stereocomplex comprising a biodegradable polymer including a first enantiomer and a second enantiomer, wherein the implantable medical device initially degrades at a first degradation rate and subsequently degrades at a second degradation rate that is faster than the first degradation rate.

17 Claims, 1 Drawing Sheet

U.S. PATENT DOCUMENTS

| | | | |
|---|---|---|---|
| 7,351,590 | B2 | 4/2008 | Martin |
| 7,368,124 | B2 | 5/2008 | Chun et al. |
| 7,541,455 | B2 | 6/2009 | Bieniarz et al. |
| 7,625,832 | B2 | 12/2009 | Purta et al. |
| 7,666,973 | B2 * | 2/2010 | Stopek ............... 528/196 |
| 7,901,705 | B2 * | 3/2011 | Roby et al. ............ 424/426 |
| 7,947,263 | B2 * | 5/2011 | Hadba et al. ............ 424/78.27 |
| 8,067,398 | B2 * | 11/2011 | Katzhendler et al. ......... 514/159 |
| 2001/0033857 | A1 | 10/2001 | Vyakarnam et al. |
| 2001/0044514 | A1 | 11/2001 | Baker et al. |
| 2002/0197645 | A1 | 12/2002 | Martin |
| 2003/0077311 | A1 | 4/2003 | Vyakarnam et al. |
| 2003/0082633 | A1 | 5/2003 | Martin et al. |
| 2004/0074759 | A1 | 4/2004 | Purta et al. |
| 2004/0118673 | A1 | 6/2004 | Sinha et al. |
| 2004/0121008 | A1 | 6/2004 | Shiraishi et al. |
| 2004/0209303 | A1 | 10/2004 | Martin |
| 2004/0249114 | A1 | 12/2004 | Swift et al. |
| 2004/0249115 | A1 | 12/2004 | Swift et al. |
| 2005/0001358 | A1 | 1/2005 | Nakazawa et al. |
| 2005/0059754 | A1 | 3/2005 | Lunt et al. |
| 2006/0127442 | A1 | 6/2006 | Helmus |
| 2006/0171985 | A1 * | 8/2006 | Richard et al. ............ 424/423 |
| 2006/0210466 | A1 | 9/2006 | Mitra et al. |
| 2006/0219710 | A1 | 10/2006 | McManus et al. |
| 2007/0043434 | A1 | 2/2007 | Meerkin et al. |
| 2007/0073033 | A1 * | 3/2007 | Sato et al. ............ 528/272 |
| 2007/0087933 | A1 | 4/2007 | Purta et al. |
| 2007/0185008 | A1 | 8/2007 | Hennink et al. |
| 2007/0235448 | A1 | 10/2007 | Lihl et al. |
| 2007/0276172 | A1 | 11/2007 | Sinha et al. |
| 2008/0078757 | A1 | 4/2008 | Lang et al. |
| 2008/0085297 | A1 * | 4/2008 | Dave et al. ............ 424/426 |
| 2008/0086199 | A1 * | 4/2008 | Dave et al. ............ 623/1.42 |
| 2008/0097074 | A1 | 4/2008 | Ouchi et al. |
| 2008/0177373 | A1 | 7/2008 | Huang et al. |
| 2008/0194805 | A1 | 8/2008 | Vignon et al. |
| 2008/0241213 | A1 | 10/2008 | Chun et al. |
| 2008/0248489 | A1 | 10/2008 | Martin |
| 2008/0264934 | A1 | 10/2008 | Moreira et al. |
| 2009/0130172 | A1 | 5/2009 | Dankers et al. |
| 2009/0214615 | A1 | 8/2009 | Zhao |
| 2009/0269480 | A1 | 10/2009 | Berglund |
| 2009/0304923 | A1 | 12/2009 | Mitra et al. |
| 2009/0318339 | A1 | 12/2009 | Katzhendler et al. |
| 2010/0004404 | A1 | 1/2010 | Suzuki et al. |
| 2010/0047324 | A1 | 2/2010 | Fritz et al. |
| 2010/0082072 | A1 | 4/2010 | Sybert et al. |

OTHER PUBLICATIONS

Slager, J., et al., "Biopolymer stereocomplexes," *Advanced Drug delivery Reviews* 55 (2003) 549-583.

Xu, H. et al., "Improvements of thermal property and crystallization behavior of PLLA based multiblock copolymer by forming stereocomplexes with PDLA oligomer," *Polymer* 47 (2006) 3922-3928.

Fujita, M. et al., "Stereocomplex formation through reorganization of PLLA and PLDA crystals," *Macromolecules* 41 (2008) 2852-2858.

Wiesbrock, F. et al., "Microwave-Assisted Polymer Synthesis: State-of-the-Art and Future Perspectives," *Macromolecular Rapid Communications*, 25 (2004) 1739-1764.

Matsumura, S., "Enzymatic Synthesis of Polyesters via Ring-Opening Polymerization", *Adv. Polym. Sci* 194 (2006) pp. 95-132.

Nalawade, Sameer P., et al., "Supercritical carbon dioxide as a green solvent for processing polymer melts: Processing aspects and applications", *Prog. Polym. Sci.* 31 (2006) pp. 19-43.

Tai, H. et al., "Putting the Fizz Into Chemistry: Applications of Supercritical Carbon Dioxide in Tissue Engineering, Drug Delivery and Synthesis of Novel Block Copolymers," *Biochem. Soc. Trans.* 35 (2007), pp. 516-521.

* cited by examiner

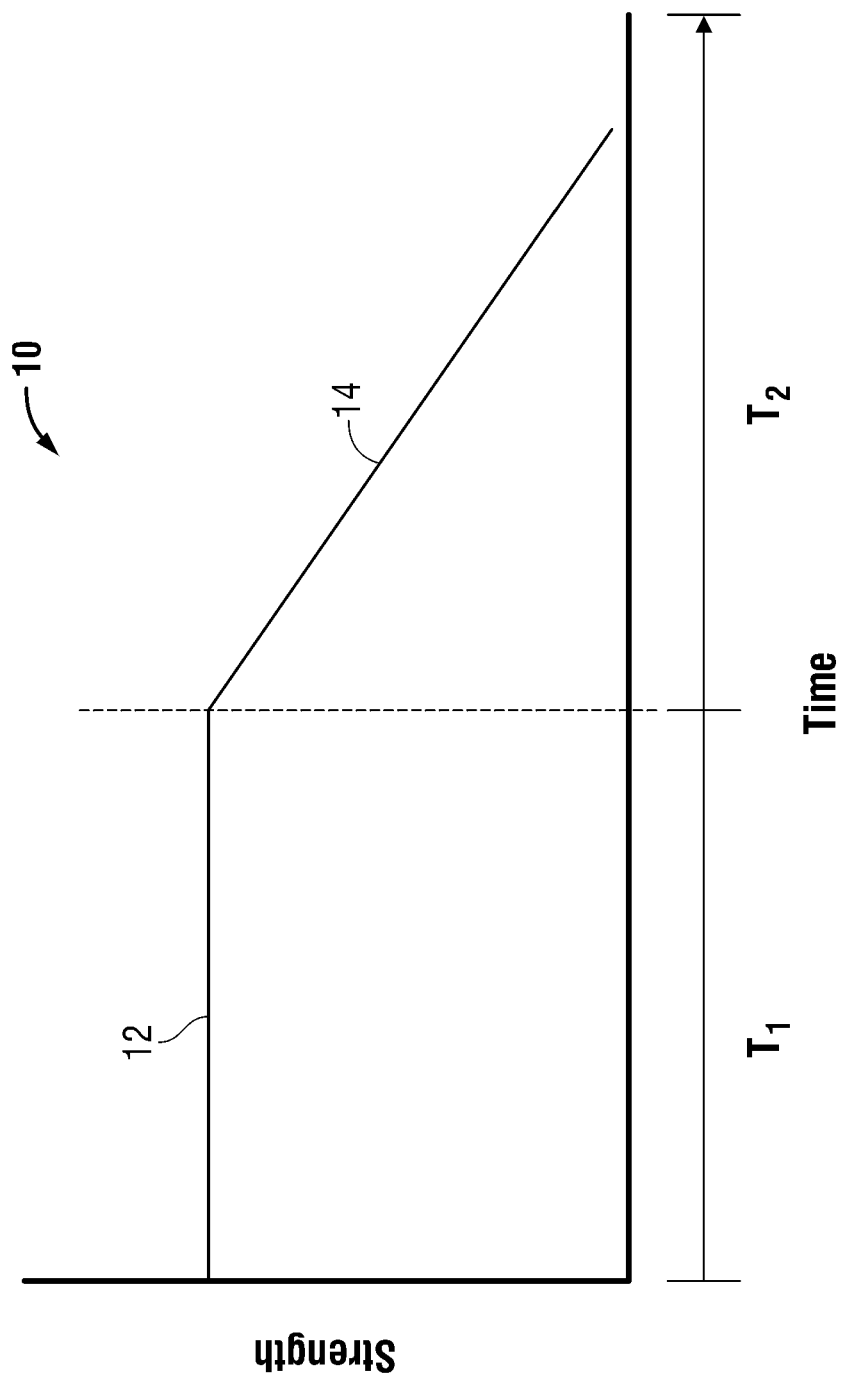

BIODEGRADABLE MATERIALS FOR ORTHOPEDIC DEVICES BASED ON POLYMER STEREOCOMPLEXES

BACKGROUND

The present disclosure relates to compositions having a predetermined degradation profile and medical devices formed from these compositions. In particular, the present disclosure relates to compositions including polymer stereocomplexes.

The use of orthopedic implants, bone grafts and bone substitute materials in orthopedic medicine is well known. While bone wounds can regenerate, fractures and other orthopedic injuries take a substantial time to heal, during which the bone is unable to support physiologic loads. It is well understood that stabilization of adjacent bone tissue may be accomplished with an implant positioned between and/or along the bone tissue. The implants may be rigid to prevent motion between the bone tissue, or flexible to allow for limited motion between the bone tissue while stabilizing the tissue.

It may be desirable to remove the implant once the healing process is complete. Non-biodegradable (e.g., metallic) implants remain permanently attached to the tissue, unless surgically removed. Certain biodegradable implants degrade at a constant rate, in which the mass and strength of the implant concurrently degrade. In certain applications a constant rate of degradation is unsuitable to achieve optimal healing, such that the rate of degradation does not coincide with the rate of healing. Improved implants with optimal degradation rates remain desirable.

SUMMARY

An implantable orthopedic medical device is disclosed. The medical device includes a biodegradable polymer stereocomplex including a biodegradable polymer comprising a first enantiomer and a second enantiomer, wherein the implantable medical device initially degrades at a first degradation rate and subsequently degrades at a second degradation rate that is faster than the first degradation rate.

In embodiments, a process is also disclosed. The process includes contacting at least one aliphatic cyclic ester with an initiator and an optional catalyst to from a biodegradable polymer comprising a first enantiomer and a second enantiomer; annealing the first and second enantiomers to form a biodegradable polymer stereocomplex; and forming an implantable medical device from the polymer stereocomplex, wherein the implantable medical device initially degrades at a first degradation rate and subsequently degrades at a second degradation rate that is faster than the first degradation rate.

BRIEF DESCRIPTION OF THE DRAWINGS

Various embodiments of the present disclosure will be described hereinbelow with reference to the figures wherein:

The FIGURE is a graph of the strength profile of a biodegradable implantable medical device of the present disclosure over time.

DETAILED DESCRIPTION

The present disclosure provides compositions and implantable medical devices formed therefrom. The compositions include a biodegradable polymer stereocomplex formed of enantiomeric polymers.

As used herein, the term "implantable medical device" denotes any type of apparatus or appliance that is totally or partly introduced into a patient's body, surgically or by medical intervention, and which is intended to remain therein. The duration of implantation may be: essentially permanent, i.e., intended to remain in place for the remaining lifespan of the patient; until the device biodegrades; or until the device is physically removed. Examples of implantable medical devices include, but are not limited to, films, foams, slit sheets, pledgets, tissue grafts, stents, stent-grafts, artificial heart valves, scaffolds, buttresses, wound dressings, meshes, vascular grafts, cochlear implants, prostheses, and combinations thereof. In embodiments, the implant is used in orthopedic applications, including, but not limited to, a rod, a pin, a screw, an anchor, a cage, combinations thereof, and the like.

As used herein, the terms "biodegradable," "bioresorbable," and "bioabsorbable" are used interchangeably and denote a characteristic according to which an implant and/or a material is resorbed by biological tissues and the surrounding fluids, and disappears in vivo after a given period of time. The time period may vary, from about several minutes to about several years or more, depending on the chemical and/or physical nature of the implant and/or of the material(s) utilized to form the implant.

As used herein, the term "enantiomer" refers to one of two mirror-image forms of an optically active molecule (e.g., polymer) that have exactly the same chemical composition. By optically active it is meant that the molecule is capable of rotating within the plane of plane-polarized light. One enantiomer rotates the plane of polarization in a clockwise direction, which is known as dextrorotatory (e.g., d-form) enantiomer. Another enantiomer rotates in a counter-clockwise direction, which is known as levorotatory (l-form) enantiomer. Thus, the two mirror-image forms (e.g., l-form and d-form) rotate in plane-polarized light equally, but in opposite directions. As used herein, a "single enantiomer" simply refers to one of the mirror image molecules in an essentially pure state.

As used herein, the term "polymer stereocomplex" denotes a stereoselective interaction between complementing stereoregular polymers (e.g., enantiomers) that interlock and form a new composite polymer with altered physical properties (e.g., higher strength profile, higher melting temperature, etc.) compared to individual homopolymers. Without being bound by any particular theory, it is believed that the polymer stereocomplex is stabilized by strong van der Waals forces, leading to an increase in the melting temperature of the polymer stereocomplex as compared to that of the individual component homopolymers. The increase in melting temperature is also reflected in improved mechanical properties of the materials formed from the polymer stereocomplexes.

Biodegradable enantiomeric polymers that may be used in accordance with the present disclosure may include polyesters, such as polylactides, including poly-L-lactide and poly-D-lactide, polyamides, polyketones, polyethers, polyacrylates, such as poly(methyl methacrylate), and combinations thereof.

The enantiomeric polyesters may be formed by ring-opening polymerization of enantiomeric cyclic aliphatic esters in the presence of an initiator and an optional catalyst, either in a solution or in bulk. In embodiments, enantiomeric cyclic aliphatic polyesters include, but are not limited to, lactide (including lactic acid, D-, L- and meso lactide), block-copolymers of L- or D-lactide with ε-caprolactone, glycolide, trimethylene carbonate, p-dioxanone, and combinations thereof, and the like.

The ring-opening polymerization of the aliphatic cyclic esters may be carried out at a temperature from about 40° C. to about 210° C., in embodiments from about 80° C. to about 200° C., in some cases in the presence of an initiator. Suitable initiators include, but are not limited to, propylene glycol; diethylene glycol; polyethylene glycol having a molecular weight from about 200 Daltons to about 600 Daltons; poly (amino acids) including proteins such as enzymes, collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. As used herein, collagen includes natural collagen such as animal derived collagen, gelatinized collagen, demineralized bone, and/or synthetic collagen such as human or bacterial recombinant collagen.

Additionally, synthetically modified natural polymers may be utilized as initiators. Such modified polymers include cellulose and polysaccharide derivatives, including alkyl celluloses, hydroxyalkyl celluloses, cellulose ethers, cellulose esters, nitrocelluloses, cellulose derivates, and chitosan. Examples of suitable cellulose derivatives include oxidized cellulose, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In embodiments, the ring-opening polymerization may occur in the presence of a catalyst. The catalyst may be a metal-based or enzyme-based catalyst. Metal-based catalysts include, but are not limited to, metal chlorides, such as stannous chloride ($SnCl_4$); metal alkoxides, including aluminum alkoxides which may be prepared by a reaction of triethylaluminum with an alcohol, zinc alkoxides, including zinc acetate, and tin alkoxides, including, stannous octoate (tin(ii) bis-(2-ethylhexanoate)); rare earth derivates, including yttrium-based catalysts (e.g., $Y(OCH_2CH_2OMe)$, $Y[N(SiMe_3)_2]_3$), halo-bridged samarium (III) complexes (e.g., $Sm(\mu\text{-}X)M(SiMe_3)_2)_2(THF)]_2$, and non-halo-bridged samarium (III) complexes (e.g., $SmCp_3$, $Sm(NC_6H_5)_3)_3$, $Sm(N(SiMe_3)_2)_3$); Lewis acid metal halogenides (e.g., $ZnCl_2$); and combinations thereof. Other suitable catalysts for ring-opening polymerization of aliphatic cyclic esters are described in Jerome et al. "Recent Advances in Synthesis of Aliphatic Polyesters by Ring-Opening Polymerization," Advanced Drug Delivery Review 60 (2008), pp. 1056-1076, the entire disclosure of which is incorporated by reference herein.

In further embodiments, the ring-opening polymerization may be carried out as an enzymatic polymerization. The enzymes thus serve as a catalyst in forming the polyester chains. Suitable enzymes to form polyesters from the ring-opening of the aliphatic cyclic esters include Pseudomonas family lipases, such as lipases from *Pseudomonas aeruginosa* (lipase PA), *Pseudomonas cepacia* (lipase PC), *Pseudomonas fluorescens* (lipase PF), as well as lipases from *Aspergillus niger* (lipase A), *Candida antarctica* (lipase CA or lipase B), *Candida cylindracea* (lipase CC), *Klebsiella oxytoca* (lipase K), *Mucor meihei* (lipase MM), cutinases such as the cutinase from *Humicola insolens*, combinations thereof, and the like.

In embodiments, the initiators and the catalysts may be immobilized onto a substrate, such as micronized or nanonized filler particles of calcium carbonate ($CaCO_3$), β-tri-calcium phosphate (β-TCP), hydroxyapatite (HA), combinations thereof, and the like. In further embodiments, the ring-opening polymerization may be carried out in the presence of microwave energy.

As would be readily appreciated by one skilled in the art, the reaction conditions for forming the enantiomer polymers of the present disclosure depend upon the starting materials and conditions used in their formation, including the starting polymeric materials, initiators, catalysts and/or enzymes, temperatures for formation, combinations thereof, and the like.

For example, in embodiments, a racemic (e.g., 50:50) mixture by weight of L and D lactide may be contacted with propylene glycol in the presence of stannous octoate. Propylene glycol may be present in an amount from about 0.001% to about 0.05% by weight of the lactide mixture, in embodiments from about 0.005% to about 0.02% by weight of the lactide mixture. Stannous octoate may be present in an amount from about 0.0001% to about 0.03% by weight of the lactide mixture, in embodiments from about 0.001% to about 0.01% by weight of the lactide mixture. The ring-opening polymerization may be carried out at a temperature from about 40° C. to about 210° C., in embodiments from about 80° C. to about 200° C.

Polymer stereocomplexes may then be formed by annealing the enantiomeric polymers. Annealing may be carried out using any suitable devices and methods. The temperature at which annealing occurs will be influenced by the materials and conditions used to form the enantiomeric polymers. Generally temperatures for annealing may be from about 80° C. to 180° C., in embodiments from about 90° C. to 150° C. In embodiments, a single-screw extruder may be used to extrude the enantiomeric polymers at a temperature from about 50° C. to about 200° C. As the extruded polymer stereocomplex leaves the extruder, the stereocomplex may be deposited into various molds or passed through shape-forming implements to be formed into implantable medical devices of various shapes and sizes.

The enantiomeric polymers may have a melting temperature from about 60° C. to 180° C., in embodiments from about 130° C. to 170° C. The resulting polymer stereocomplex may have a melting temperature from about 100° C. to 280° C., in embodiments from about 150° C. to 250° C.

As discussed above, the increased melting temperature of the polymer stereocomplex may be attributable to an increase in the stability of the crystalline domain in the blend. Implantable medical devices formed from the polymer stereocomplex according to present disclosure thus display a higher mechanical strength profile during an initial time period due to the increase in stability of the crystalline domain of the stereocomplex.

Medical devices formed from the polymer stereocomplexes of the present disclosure have a dual-stage degradation profile, as illustrated by plot 10 in the FIGURE. Following implantation of the medical device and/or exposure to bodily fluids, including water, blood, mucous, saline, dextrose, and the like, the medical device undergoes degradation. Due to its higher melting temperature, the polymer stereocomplex degrades at multiple rates, including a first predetermined rate during a first degradation period 12. During the first period 12, the polymer stereocomplex degrades into its constituent enantiomeric polymers, thereby still retaining its mechanical strength as illustrated by a substantially unchanged strength profile during the first period 12 of the FIGURE.

After the stereocomplex has substantially degraded, the enantiomeric polymers begin to degrade during a second degradation period 14. During the second period 14, the enantiomeric polymers degrade at a second predetermined rate, which is faster than that of the stereocomplex, due to the lower melting point of the constituent polymers. The enantiomeric polymers are reduced from a solid or gel to a liquid following interaction with bodily fluids located at the site of implantation, thereby resulting in strength and mass loss of the medical device. As a result, the mechanical strength of the implant decreases at a faster rate during the second period 14.

The first rate of degradation (i.e., first time period 12) may be from about 30 days to about 730 days, in embodiments, from about 60 days to about 365 days. The second rate of degradation (i.e., second time period 14) may be from about 30 days to about 1,095 days, in embodiments, from about 60 days to about 730 days.

The polymer stereocomplex may be used to form orthopedic implants including, but not limited to, spinal fusion interbody cages, intramedullary nails, screws, plates, bone grafts, combinations thereof, and the like. In embodiments, the polymer stereocomplex may be used to form a coating on the orthopedic implants.

In addition to providing tissue support, the implantable medical devices of the present disclosure may further be used for delivery of a bioactive agent. Thus, in some embodiments, at least one bioactive agent may be provided in or on the medical device.

The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present medical device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents include local anesthetics, non-steroidal antifertility agents, parasympathomimetic agents, psychotherapeutic agents, tranquilizers, decongestants, sedative hypnotics, steroids, sulfonamides, sympathomimetic agents, vaccines, vitamins, antimalarials, anti-migraine agents, antiparkinson agents such as L-dopa, anti-spasmodics, anticholinergic agents (e.g., oxybutynin), antitussives, bronchodilators, cardiovascular agents such as coronary vasodilators and nitroglycerin, alkaloids, analgesics, narcotics such as codeine, dihydrocodeinone, meperidine, morphine and the like, non-narcotics such as salicylates, aspirin, acetaminophen, d-propoxyphene and the like, opioid receptor antagonists, such as naltrexone and naloxone, anti-cancer agents, anti-convulsants, anti-emetics, antihistamines, antiinflammatory agents such as hormonal agents, hydrocortisone, prednisolone, prednisone, non-hormonal agents, allopurinol, indomethacin, phenylbutazone and the like; prostaglandins and cytotoxic drugs, chemotherapeutics, estrogens, antibacterials, antibiotics, anti-fungals, anti-virals, anticoagulants, anticonvulsants, antidepressants, antihistamines, and immunological agents.

Other examples of suitable bioactive agents also include viruses and cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens), somatostatin, antigens, blood coagulation factors, growth factors (e.g., nerve growth factor, insulin-like growth factor), bone morphogenic proteins, TGF-B, protein inhibitors, protein antagonists, and protein agonists, nucleic acids, such as antisense molecules, DNA, RNA, RNAi, oligonucleotides, polynucleotides, and ribozymes.

It will be appreciated that the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. An implantable orthopedic medical device comprising: a biodegradable polymer stereocomplex comprising a biodegradable polymer comprising a first enantiomer and a second enantiomer, the biodegradable polymer is immobilized on a filler particle prior to being contacted with an initiator and an optional catalyst, wherein the implantable medical device initially degrades at a first degradation rate and subsequently degrades at a second degradation rate that is faster than the first degradation rate.

2. The implantable medical device according to claim 1, wherein the biodegradable polymer is selected from the group consisting of polyesters, polyamides, polyketones, polyethers, polyacrylates, and combinations thereof.

3. The implantable medical device according to claim 2, wherein the biodegradable polymer is selected from the group consisting of lactides and block-copolymers of lactides with at least one other component selected from the group consisting of ε-caprolactone, glycolide, trimethylene carbonate, p-dioxanone, and combinations thereof.

4. The implantable medical device according to claim 1, wherein the initiator is selected from the group consisting of propylene glycol, diethylene glycol, polyethylene glycol, collagen, elastin, fibrin, fibrinogen, silk, albumin, peptides, hyaluronic acid, dextran, alginate, chitin, chitosan, cellulose, glycosaminoglycan, gut, and combinations thereof.

5. The implantable medical device according to claim 1, wherein the catalyst is selected from the group consisting of a metal alkoxide, a rare earth complex, and an enzyme.

6. The implantable medical device according to claim 1, wherein the catalyst is selected from the group consisting of aluminum alkoxide, zinc alkoxide, tin alkoxide, tin chloride, and combinations thereof.

7. The implantable medical device according to claim 1, wherein the polymer stereocomplex is formed by annealing the first and second enantiomers at a temperature from about 60° C. to about 180° C.

8. The implantable medical device according to claim 1, wherein the polymer stereocomplex degrades at the first degradation rate during a first period of time and the first and second enantiomers degrade at the second degradation rate during a second period of time.

9. The implantable medical device according to claim 8, wherein the first period of time is from about 30 days to about 730 days and the second period of time is from about 30 days to about 1,095 days.

10. A process comprising:
contacting a biodegradable polymer immobilized on a filler particle with an initiator and an optional catalyst comprising a first enantiomer and a second enantiomer;
annealing the first and second enantiomers to form a biodegradable polymer stereocomplex; and
forming an implantable medical device from the polymer stereocomplex,
wherein the implantable medical device initially degrades at a first degradation rate and subsequently degrades at a second degradation rate that is faster than the first degradation rate.

11. The process according to claim 10, wherein the biodegradable polymer is selected from the group consisting of polyesters, polyamides, polyketones, polyethers, polyacrylates, and combinations thereof.

12. The process according to claim 11, wherein the biodegradable polymer is selected from the group consisting of lactides and block-copolymers of lactides with at least one other component selected from the group consisting of ε-caprolactone, glycolide, trimethylene carbonate, p-dioxanone, and combinations thereof.

13. The process according to claim 10, wherein the initiator is selected from the group consisting of propylene glycol, diethylene glycol, polyethylene glycol, collagen, elastin, fibrin, fibrinogen, silk, albumin, peptides, hyaluronic acid, dextran, alginate, chitin, chitosan, cellulose, glycosaminoglycan, gut, and combinations thereof.

14. The process according to claim 10, wherein the catalyst is selected from the group consisting of aluminum alkoxide, zinc alkoxide, tin alkoxide, tin chloride, and combinations thereof.

15. The process according to claim 10, wherein the annealing is performed at a temperature from about 80° C. to about 180° C.

16. The process according to claim 10, wherein the polymer stereocomplex degrades at the first degradation rate over a period of time from about 30 days to about 730 days and the first and second enantiomers degrade at the second degradation rate over a period of time from about 30 days to about 1,095 days.

17. The process according to claim 10, further comprising exposing the biodegradable polymer, the initiator and the optional catalyst to microwave energy.

* * * * *